(12) United States Patent
Buckley et al.

(10) Patent No.: US 7,312,352 B2
(45) Date of Patent: Dec. 25, 2007

(54) METHOD OF PREPARING ESTER-SUBSTITUTED DIARYL CARBONATES

(76) Inventors: Paul William Buckley, 60 Paradowski Rd., Scotia, NY (US) 12302; James Silva, 20 Nottingham Way North, Clifton Park, NY (US) 12065; David Dardaris, 64 Middle St., Ballston Spa, NY (US) 12020

( * ) Notice: Subject to any disclaimer, the term of this patent is extended or adjusted under 35 U.S.C. 154(b) by 556 days.

(21) Appl. No.: 10/984,318

(22) Filed: Nov. 8, 2004

(65) Prior Publication Data

US 2006/0025622 A1 Feb. 2, 2006

Related U.S. Application Data

(60) Provisional application No. 60/598,336, filed on Aug. 2, 2004.

(51) Int. Cl.
*C07C 69/96* (2006.01)
(52) U.S. Cl. ...................... 558/274; 558/270
(58) Field of Classification Search ............... 558/270, 558/273, 274
See application file for complete search history.

(56) References Cited

U.S. PATENT DOCUMENTS

| | | | |
|---|---|---|---|
| 4,323,668 A | 4/1982 | Brunelle | |
| 5,091,591 A | 2/1992 | Cipullo | |
| 5,151,491 A | 9/1992 | Sakashita et al. | |
| 5,276,129 A | 1/1994 | Sakashita et al. | |
| 5,525,701 A | 6/1996 | Tominari et al. | |
| 5,696,222 A | 12/1997 | Kaneko et al. | |
| 6,177,536 B1 | 1/2001 | Anamizu et al. | |
| 6,252,036 B1 | 6/2001 | Hatono et al. | |
| 6,300,459 B1 | 10/2001 | Kaneko et al. | |
| 6,303,734 B1 | 10/2001 | Funakoshi et al. | |
| 6,399,739 B1 | 6/2002 | McCloskey et al. | |
| 6,403,754 B1 | 6/2002 | McCloskey et al. | |
| 6,410,777 B1 | 6/2002 | Kaneko et al. | |
| 6,417,291 B1 | 7/2002 | Kaneko et al. | |
| 6,420,512 B1 | 7/2002 | McCloskey et al. | |
| 6,420,588 B1 * | 7/2002 | McCloskey et al. | 558/274 |
| 6,469,192 B1 | 10/2002 | Burnell et al. | |
| 6,500,914 B1 | 12/2002 | Brack et al. | |
| 6,506,871 B1 | 1/2003 | Silvi et al. | |
| 6,518,391 B1 | 2/2003 | McCloskey et al. | |
| 6,525,163 B1 | 2/2003 | Brack et al. | |
| 6,548,623 B2 * | 4/2003 | Brunelle et al. | 528/196 |
| 6,590,068 B2 | 7/2003 | Brack et al. | |
| 6,600,004 B1 | 7/2003 | McCloskey et al. | |
| 6,653,434 B2 | 11/2003 | Brack et al. | |
| 6,706,846 B2 | 3/2004 | Brack et al. | |
| 6,710,156 B2 | 3/2004 | Whitney et al. | |
| 6,723,823 B2 | 4/2004 | McCloskey et al. | |
| 6,734,277 B2 | 5/2004 | Brack et al. | |
| 6,747,119 B2 | 6/2004 | Brack et al. | |
| 6,870,025 B2 * | 3/2005 | McCloskey et al. | 528/196 |
| 6,891,015 B2 * | 5/2005 | Burnell et al. | 528/196 |
| 2002/0132957 A1 | 9/2002 | Brack et al. | |
| 2003/0060649 A1 | 3/2003 | Burnell et al. | |
| 2004/0068086 A1 | 4/2004 | Day et al. | |
| 2004/0087756 A1 | 5/2004 | Ramesh et al. | |

FOREIGN PATENT DOCUMENTS

| | | |
|---|---|---|
| JP | 5009282 A2 | 1/1993 |
| JP | 10-101786 A2 | 4/1998 |
| JP | 10-101787 A2 | 4/1998 |
| JP | 11-302228 | 11/1999 |
| JP | 2000129112 | 5/2000 |
| JP | 2002-309015 A2 | 10/2002 |
| WO | WO 03/040208 A1 | 5/2003 |
| WO | WO 03/106149 A1 | 12/2003 |

* cited by examiner

*Primary Examiner*—Golam M. M. Shameem
(74) *Attorney, Agent, or Firm*—Marina Larson & Associates, LLC

(57) ABSTRACT

The present invention relates to an interfacial method of preparing ester-substituted diaryl carbonates. The method includes the steps of: forming a reaction mixture comprising phosgene, an ester-substituted phenol, an organic solvent, and a catalyst selected from the group consisting of a tertiary amine catalyst and a phase transfer catalyst, said reaction mixture having an organic phase and an aqueous phase, wherein said aqueous phase has a brine strength; allowing the reaction mixture to react wherein during the reaction, (i) the aqueous phase has a pH, and the pH is adjusted, if necessary, by the addition of an alkali metal hydroxide solution in amounts such that the pH is greater than or equal to 9.0 during at least some portion of the reaction, and (ii) the brine strength of the aqueous phase is adjusted, if necessary, by varying the concentration of the alkali metal hydroxide solution being added to maintain the pH such that the brine strength is between 15% and a saturated brine solution during at least some portion of the reaction: thereby forming an ester-substituted diaryl carbonate, wherein the reaction mixture is formed with less than 15% water of formulation, and wherein the brine strength is maintained at or above 15% and the pH is maintained at or above 9 for a sufficient portion of the process that the ester-substituted diaryl carbonate is formed with a conversion of at least 90% and a selectivity of at least 98%.

21 Claims, 5 Drawing Sheets

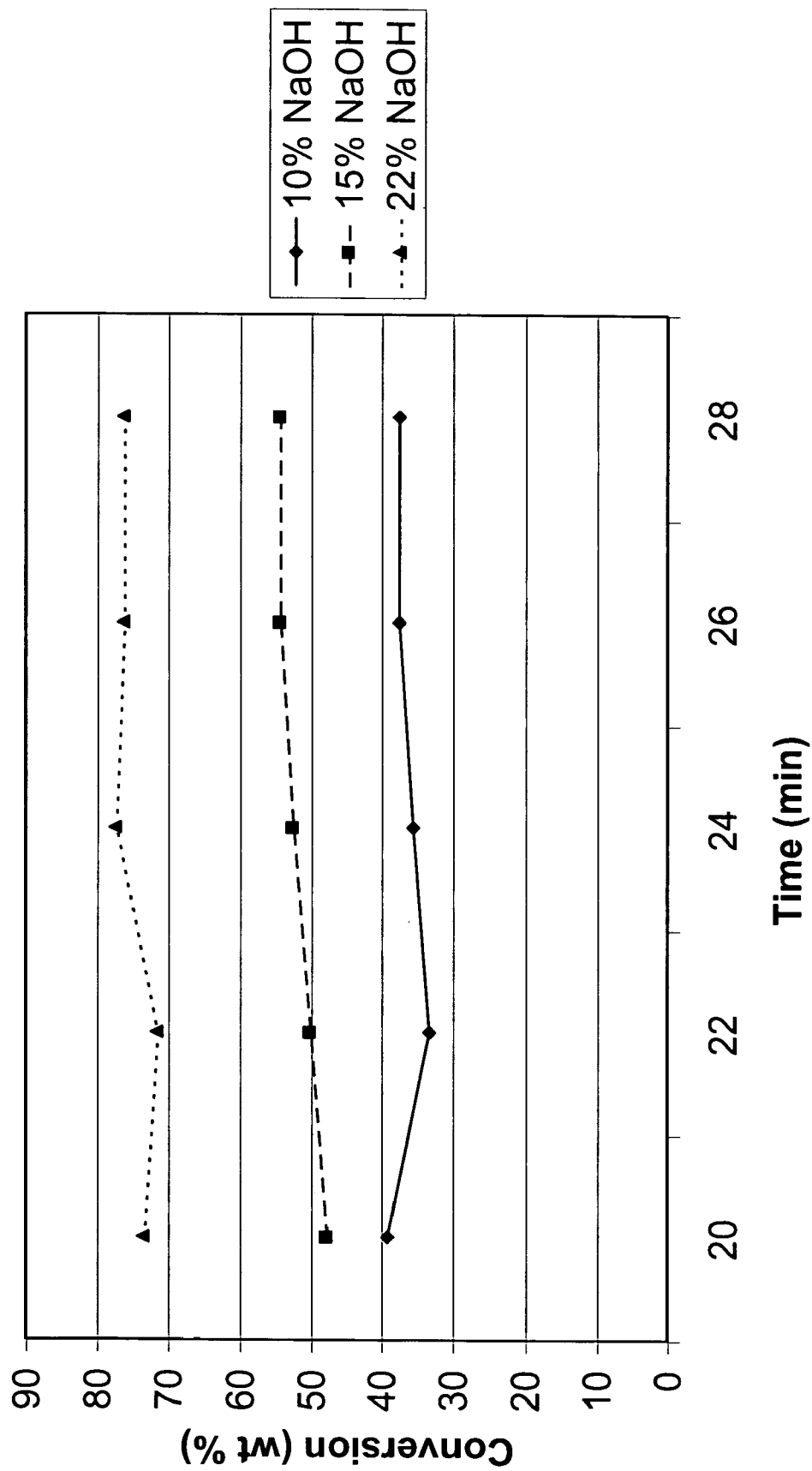
Figure 1: Conversion at pH 8 and Various Brine Concentrations

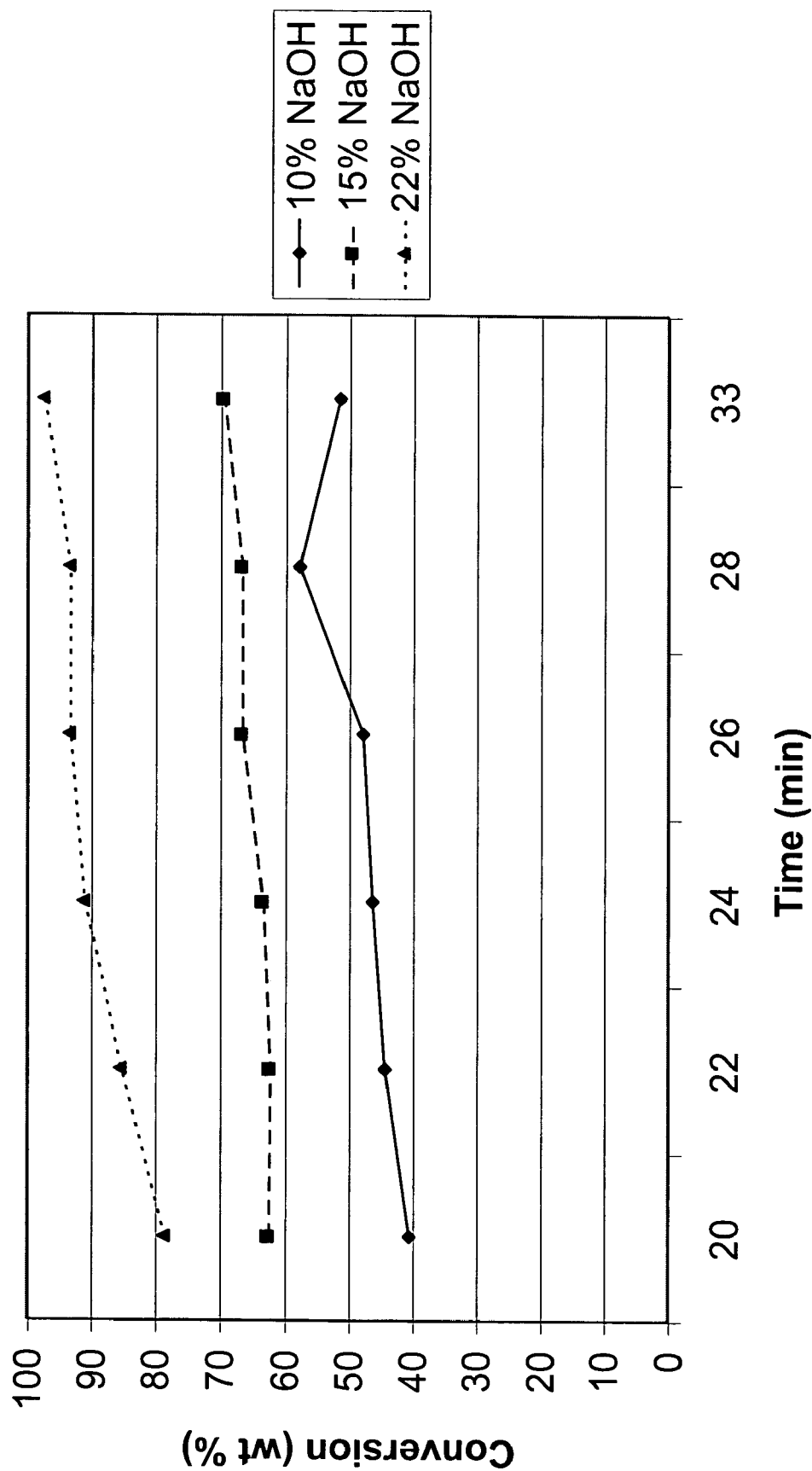

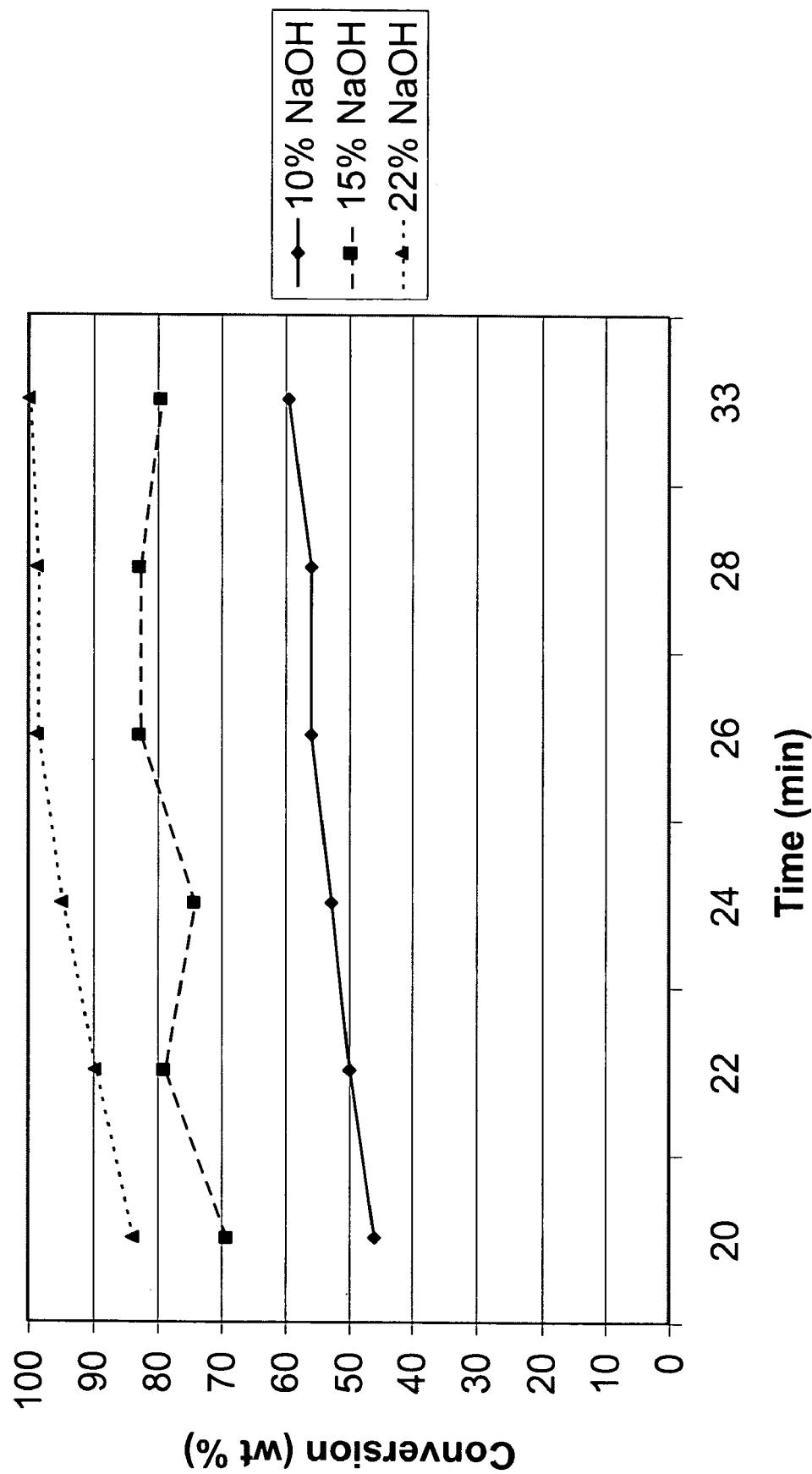

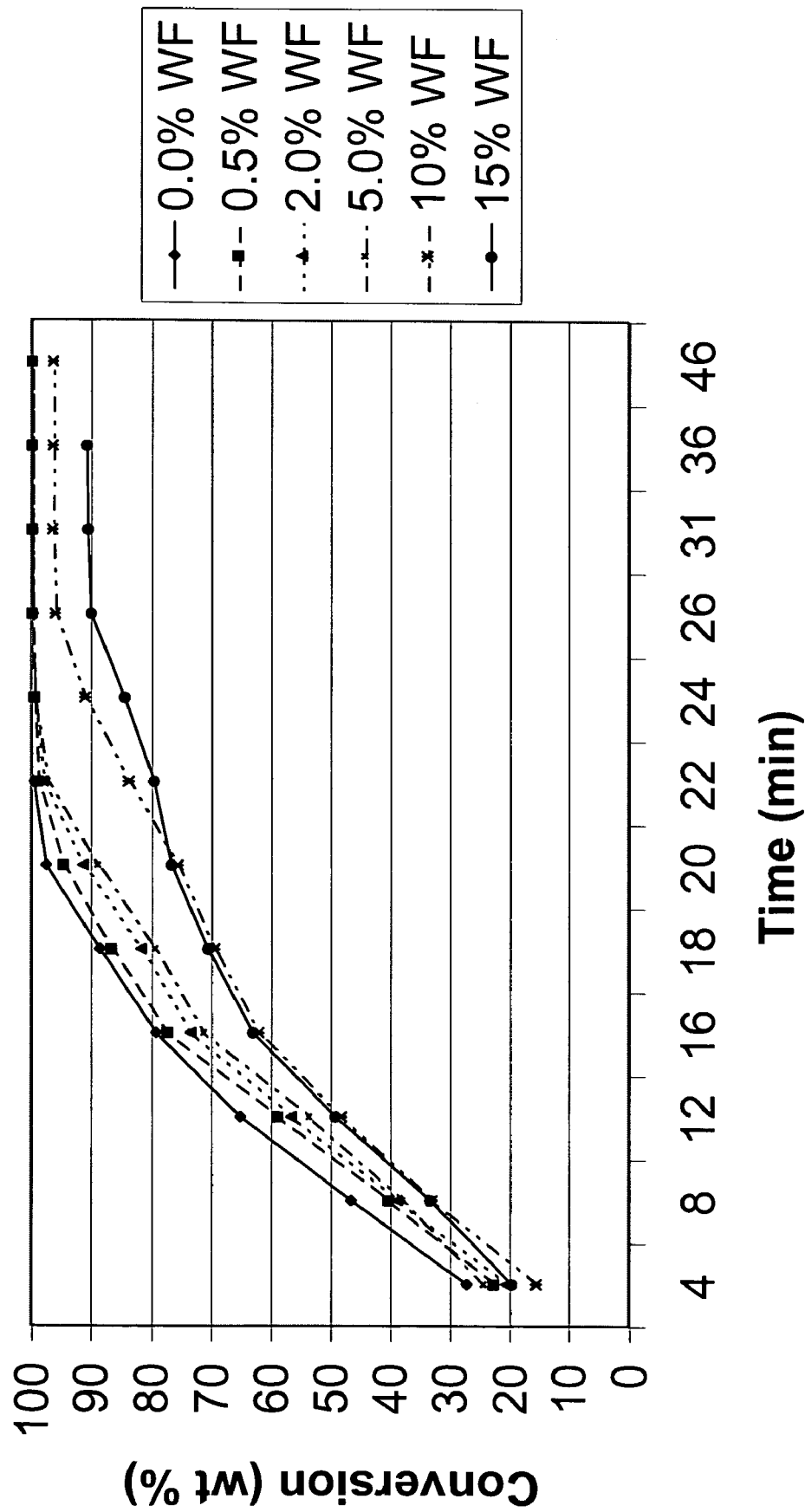

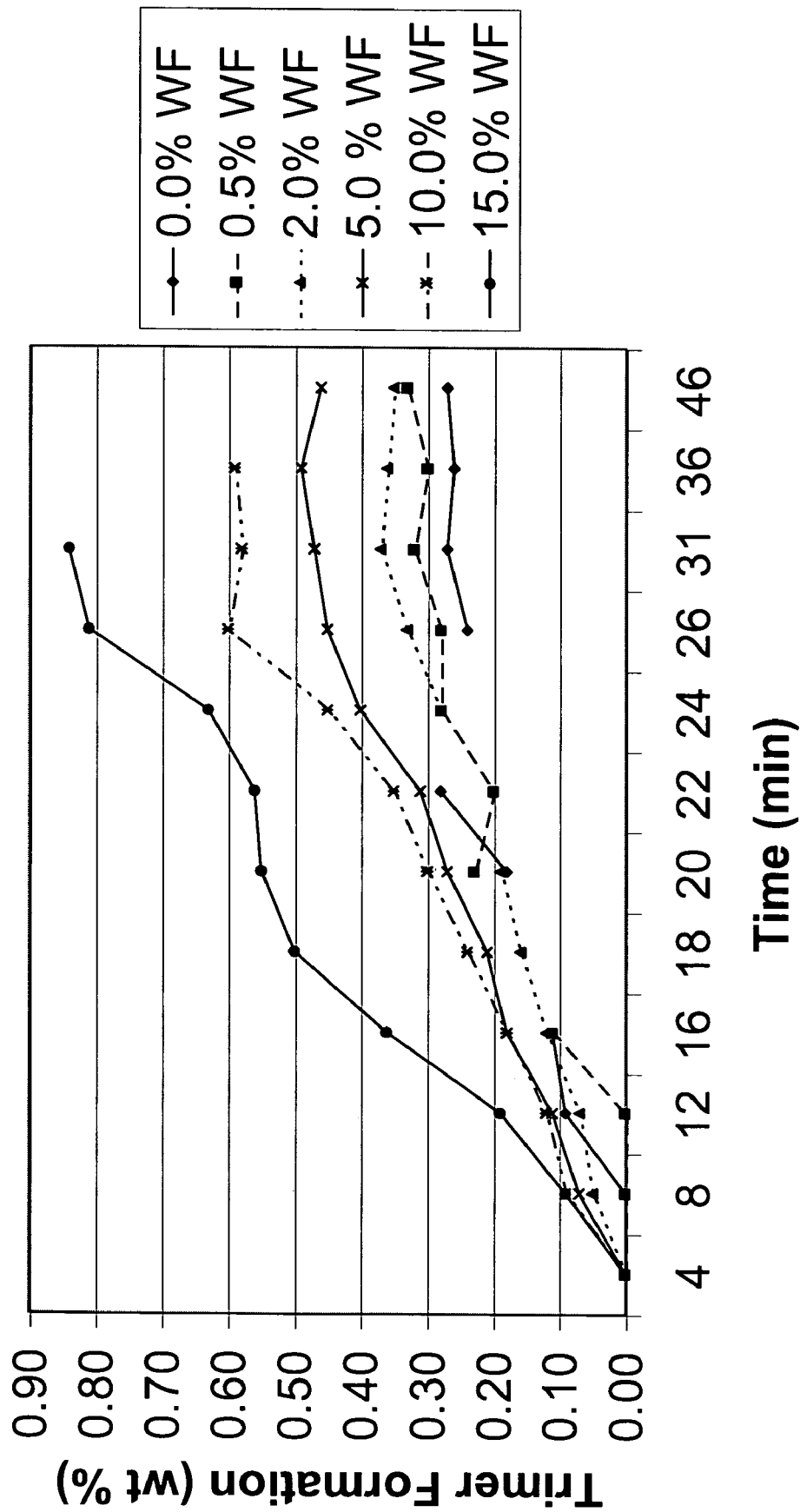
Figure 5: Effect of Water of Formulation (WF) on Selectivity (% Trimer Formation)

METHOD OF PREPARING ESTER-SUBSTITUTED DIARYL CARBONATES

CROSS-REFERENCE TO RELATED APPLICATIONS

This application claims the benefit of U.S. provisional application 60/598,336 filed on Aug. 2, 2004, which is incorporated herein by reference in its entirety.

BACKGROUND OF THE INVENTION

This invention relates to a method of making ester-substituted diaryl carbonates. Ester-substituted diaryl carbonates such as bis-methyl salicyl carbonate (BMSC) have proven to be useful starting materials in the preparation of polycarbonates via the melt reaction of a diaryl carbonate with aromatic dihydroxy compounds. See for example, U.S. Pat. No. 4,323,668 in which rates of polymerization of bis-methyl salicyl carbonate with bisphenol A were shown to be higher than the corresponding rates of polymerization of bisphenol A with an unsubstituted diaryl carbonate, diphenyl carbonate. Notwithstanding the simplicity of its structure there are few reported preparations of ester-substituted diaryl carbonates.

A classical preparation of diaryl carbonates involves the reaction of a hydroxy aromatic compound such as phenol with phosgene gas in a two phase reaction system comprising water of formulation, an acid acceptor such as sodium hydroxide and a solvent such as methylene chloride or chloroform. Typical interfacial conditions used to prepare diphenyl carbonate (DPC) utilize water, also known as water of formulation, and methylene chloride phases, sodium hydroxide as a pH control measure and triethylamine as a catalyst. Under such conditions it is possible to convert phenol to DPC in essentially quantitative yield. However, application of these same conditions to ester-substituted phenols such as methyl salicylate results in only modest conversion of this ester-substituted phenol to the corresponding diaryl carbonate. Even the use of as much as 20 percent excess phosgene does not result in conversion of more than 70% to 75% of methyl salicylate to the bis methyl salicyl carbonate.

It would be desirable, therefore, to discover means for the efficient preparation of ester-substituted diaryl carbonates generally, and in particular it would be desirable to discover a highly efficient means of preparing bis-methyl salicyl carbonate from methyl salicylate and phosgene.

SUMMARY OF THE INVENTION

Applicants have discovered a superior process for the production of ester-substituted diaryl carbonates. The present invention provides a method of preparing an ester-substituted diaryl carbonate, wherein one embodiment the method comprises the steps of:

(a) forming a reaction mixture comprising phosgene, an ester-substituted phenol, an organic solvent, and a catalyst selected from the group consisting of a tertiary amine catalyst and a phase transfer catalyst, said reaction mixture having an organic phase and an aqueous phase, wherein said aqueous phase has a brine strength, (b) allowing the reaction mixture to react wherein during the reaction,
  (i) the aqueous phase has a pH, and the pH is adjusted, if necessary, by the addition of an alkali metal hydroxide solution in amounts such that the pH is greater than or equal to 9.0 during at least some portion of the reaction, and
  (ii) the brine strength of the aqueous phase is adjusted, if necessary, by varying the concentration of the alkali metal hydroxide solution being added to maintain the pH such that the brine strength is between 15% and a saturated brine solution during at least some portion of the reaction, thereby forming an ester-substituted diaryl carbonate, wherein the reaction mixture is formed with less than 15% water of formulation, and wherein the brine strength is maintained at or above 15% and the pH is maintained at or above 9 for a sufficient portion of the process that the ester-substituted diaryl carbonate is formed with a conversion of at least 90% and a selectivity of at least 98%.

The present invention is an improvement over the prior art. It has been found that the process of the present invention allows for high conversion and selectivity with the use of a near 1:2 molar ratio of phosgene to ester-substituted phenol. The present invention provides a novel process of reacting phosgene and ester-substituted phenol in a high pH brine environment that is substantially free of water of formulation. By reducing and even eliminating the water of formulation that is typically used in such a process and introducing a high pH brine solution to the reaction mixture, the amount of phosgene required is minimized while maximizing conversion and selectivity of the ester-substituted phenol to the product ester-substituted diaryl carbonate.

BRIEF DESCRIPTION OF THE DRAWING

FIG. 1: Shows the results of examples 12-14 run at a pH value of 8

FIG. 2: Shows the results of examples 15-17 run at a pH value of 9

FIG. 3: Shows the results of examples 18-20 run at a pH value of 10

FIG. 4: Shows the effect of water of formulation on conversion

FIG. 5: Shows the effect of water of formulation on selectivity

DETAILED DESCRIPTION OF THE INVENTION

The present invention may be understood more readily by reference to the following detailed description of preferred embodiments of the invention and the examples included therein. In the specification and the claims which follow, reference will be made to a number of terms which shall be defined to have the following meanings:

The singular forms "a", "an", and "the" include plural referents unless the context clearly dictates otherwise.

"Optional" or "optionally" means that the subsequently described event or circumstance may or may not occur, and that the description includes instances where the event occurs and instances where it does not.

"Polycarbonate" refers to polycarbonates incorporating repeat units derived from at least one dihydroxy aromatic compound and includes copolyestercarbonates, for example a polycarbonate comprising repeat units derived from resorcinol, bisphenol A, and dodecandioic acid. Nothing in the description and claims of this application should be taken as limiting the polycarbonate to only one dihydroxy residue unless the context is expressly limiting. Thus, the application encompasses copolycarbonates with residues of 2, 3, 4, or more types of dihydroxy compounds.

"Selectivity" refers to the amount of ester-substituted phenol that is converted to product ester-substituted diaryl carbonate rather than to undesired byproducts. It is calculated as (mole ester-substituted phenol converted to mole ester-substituted diaryl carbonate/total mole of ester-substituted phenol consumed).

"Conversion" refers to the total amount of ester-substituted diaryl carbonate formed from the raw material ester-substituted phenol. It is calculated as (weight ester-substituted diaryl carbonate/(weight ester-substituted diaryl carbonate+weight ester-substituted phenol+weight by-product)).

"Water of formulation" is also known as free water of formulation and is calculated in the examples as the weight percent of water based on the weight percent of methylene chloride in formulation. Water of formulation does not include water that is added to a reaction mixture as part of an aqueous sodium hydroxide solution.

Numerical values in the specification and claims of this application reflect average values. Furthermore, the numerical values should be understood to include numerical values which are the same when reduced to the same number of significant figures and numerical values which differ from the stated value by less than the experimental error of the measurement technique used in the present application to determine the value.

In the present invention it has been discovered that ester-substituted phenols such as methyl salicylate are efficiently converted to ester-substituted diaryl carbonates such as bis-methyl salicyl carbonate under mild reaction temperatures while maximizing conversion and selectivity while minimizing byproduct formation and the use of excess phosgene. One embodiment of the present invention provides a method of preparing ester-substituted diaryl carbonates comprising the steps of:

(a) forming a reaction mixture comprising phosgene, an ester-substituted phenol, an organic solvent, and a catalyst selected from the group consisting of a tertiary amine catalyst and a phase transfer catalyst, said reaction mixture having an organic phase and an aqueous phase, wherein said aqueous phase has a brine strength, (b) allowing the reaction mixture to react wherein during the reaction,
  (i) the aqueous phase has a pH, and the pH is adjusted, if necessary, by the addition of an alkali metal hydroxide solution in amounts such that the pH is greater than or equal to 9.0 during at least some portion of the reaction, and
  (ii) the brine strength of the aqueous phase is adjusted, if necessary, by varying the concentration of the alkali metal hydroxide solution being added to maintain the pH such that the brine strength is between 15% and a saturated brine solution during at least some portion of the reaction,
thereby forming an ester-substituted diaryl carbonate,
wherein the reaction mixture is formed with less than 15% water of formulation, and wherein the brine strength is maintained at or above 15% and the pH is maintained at or above 9 for a sufficient portion of the process that the ester-substituted diaryl carbonate is formed with a conversion of at least 90% and a selectivity of at least 98%.

The Ester-Substituted Diaryl Carbonate:

In one aspect of the present invention a method is provided for the preparation of ester-substituted diaryl carbonates having structure I,

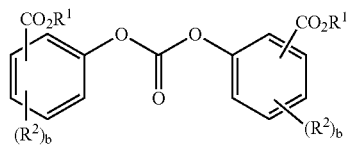

wherein $R^1$ is independently at each occurrence a $C_1$-$C_{20}$ alkyl radical, $C_4$-$C_{20}$ cycloalkyl radical, or $C_4$-$C_{20}$ aromatic radical; $R^2$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and b is independently at each occurrence an integer 0-4.

Examples of ester-substituted diaryl carbonates which may be prepared using the method of the present invention include bis-methyl salicyl carbonate (CAS Registry No. 82091-12-1), bis-ethyl salicyl carbonate, bis-propyl salicyl carbonate, bis-butyl salicyl carbonate, bis-benzyl salicyl carbonate, bis-methyl 4-chlorosalicyl carbonate and the like. Typically bis-methyl salicyl carbonate is preferred for use in melt polycarbonate synthesis due to its lower molecular weight and higher vapor pressure.

The Ester-Substituted Phenol:

The ester-substituted phenol used in accordance with the present invention is at least one compound selected from among phenols having structure II,

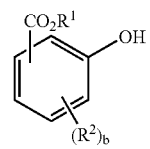

wherein $R^1$ and $R^2$ are defined as in structure I and b is an integer 0-4.

Examples of ester-substituted phenols which may serve as starting materials for the method of the present invention include phenyl salicylate, methyl salicylate, ethyl salicylate, propyl salicylate, butyl salicylate, benzyl salicylate, methyl 4-chloro salicylate and the like. Typically, methyl salicylate is preferred.

Catalysts:

It has been found that a tertiary amine catalyst or a phase transfer catalyst or both may be used in accordance with the method of this invention. These catalysts have been found to accelerate the formation of ester-substituted diaryl carbonate product and to act to minimize the presence of the intermediate ester-substituted phenyl chloroformate in the product.

Phase Transfer Catalyst:

Suitable phase transfer catalysts are widely available and include quaternary ammonium salts of aliphatic amines, quaternary ammonium salts of aromatic amines, quaternary phosphonium salts, sulfonium salts, polyethers and the like. Quaternary ammonium salts of aromatic amines are illustrated by N-benzyl pyridinium chloride, N-benzyl 4-N',N'-dimethylamino pyridinium chloride and the like. Quaternary ammonium salts include hexaalkyl guanidinium compounds such as hexaethyl guanidinium chloride. Quaternary phosphonium salts are illustrated by tetrabutyl phosphonium acetate and the like. Sulfonium salts are illustrated by trimethyl sulfonium chloride and the like. Polyethers are illustrated by polyethylene glycol and crown ethers such as 18-crown-6 and the like.

In one embodiment of the present invention the phase transfer catalyst is a quaternary ammonium compound having structure III,

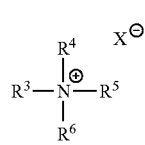

wherein $R^3$-$R^6$ are independently a $C_1$-$C_{20}$ alkyl radical, $C_4$-$C_{20}$ cycloalkyl radical, or a $C_4$-$C_{20}$ aryl radical, and $X^-$ is an organic or inorganic anion. Suitable anions $X^-$ include hydroxide, halide, carboxylate, sulfonate, sulfate, carbonate and bicarbonate.

Where $X^-$ is a polyvalent anion such as carbonate or sulfate it is understood that the positive and negative charges in structure III are properly balanced. For example, where $R^3$-$R^6$ in structure III are each methyl groups and $X^-$ is carbonate, it is understood that $X^-$ represents $\frac{1}{2}(CO_3^{-2})$.

A non-limiting list of quaternary ammonium compounds having structure III and which are suitable for use as phase transfer catalysts according to the method of the present invention are illustrated by tetramethyl ammonium hydroxide, tetrabutyl ammonium hydroxide, tetramethyl ammonium acetate, tetramethyl ammonium formate, tetrabutyl ammonium acetate, methyl tributyl ammonium chloride, tetramethyl ammonium hydroxide, tetrabutyl ammonium chloride and decyl trimethyl ammonium chloride. Methyl tributyl ammonium chloride is frequently preferred.

The amount of phase transfer catalyst employed is in a range between 0.1 and 2 mole percent catalyst, and preferably between 0.25 and 1.0 mole percent catalyst per mole of ester-substituted phenol employed.

Tertiary Amine Catalyst:

In another embodiment of the present invention a tertiary amine is included as a catalyst for the formation of ester-substituted diaryl carbonates. The tertiary amine used as a catalyst of the present invention are of formula IV:

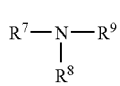

wherein each $R^7$, $R^8$, and $R^9$ are independently a $C_1$-$C_{18}$ alkyl group, a $C_3$-$C_{18}$ cycloalkyl group, or $R^7$, $R^8$, and $R^9$ together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof.

A non-limiting list of tertiary amines suitable for use as catalysts according to the method of the present invention are illustrated by triethylamine, diisopropyl ethyl amine, tributylamine, and 1,4-diazabicyclooctane. Triethylamine is frequently preferred. Typically, the amount of tertiary amine catalyst used is in a range between 0.01 mole percent and 1 mole percent. When formulating the reaction mixture preferably between 0.01 mole percent and 0.09 mole triethylamine is added based upon the total number of moles of ester-substituted phenol employed in the reaction mixture.

The Process:

The method of the present invention has the unexpected finding that by minimizing and even eliminating water of formulation and controlling the pH and the brine strength of the reaction mixture dramatically improves the conversion and selectivity of ester-substituted phenols to product ester-substituted diaryl carbonates when the phenols are contacted with phosgene.

According to the method of the present invention an ester-substituted phenol is contacted with phosgene in an amount equivalent from 0.75 to 1.00, more preferably 0.55 to 1.00, and still more preferably 0.50 to 1.00 moles of phosgene to moles of ester-substituted phenol. The reaction of the phosgene and the ester-substituted phenol takes place in the presence of an organic solvent, and a catalyst selected from the group consisting of a tertiary amine catalyst and a phase transfer catalyst.

This contact takes place in an environment that is preferably substantially free of water of formulation. It has herein been found that such water of formulation has the effect of hydrolyzing the phosgene and the intermediate carbonate wherein such hydrolysis renders a portion of the phosgene unavailable for activated diaryl carbonate formation. Hence, the more water of formulation the more phosgene that is required for conversion of the ester-substituted phenol to the product ester-substituted diaryl carbonate. It has been found that up to 15% water of formulation may be present in the reaction mixture while still achieving 90% conversion and 98% selectivity. However, conversion and selectivity are improved when the reaction mixture contains less than 10%, for example less than 5% water of formulation. It is most preferable that the reaction mixture comprise no free water of formulation.

It will be appreciated that industrial solvents may contain water and this is not "water of formulation." Similarly some water may be presented provided that caustic is added or available for brine formation within a short period of time (e.g. less than five minutes and preferably less than one minute) after addition of phosgene commences. In contrast to a reaction that is free of water of formulation comparative example 1 shows a reaction wherein water of formulation is present in the reaction mixture and NaOH addition occurs at a rate of 6.72 g/min over a period of 25 minutes during the phosgene addition. The result is only 54% conversion as a result of substantial hydrolysis during the initial portion of the reaction. (See Table 1 in the example section).

The brine strength and pH of the reaction mixture are controlled by the addition of an acid scavenger, preferably a metal hydroxide, and still more preferably an alkali metal hydroxide solution. Suitable alkali metal hydroxides include sodium hydroxide, potassium hydroxide, lithium hydroxide, calcium hydroxide, and magnesium hydroxide. An aqueous solution of sodium hydroxide containing from 5 to 50 percent by weight NaOH is preferred.

The pH and brine strength are typically maintained throughout the reaction of the reaction mixture at their desired levels. Several methods of measuring and maintaining the brine strength and pH of the solution may be employed and are not particularly limited. Typically the pH and brine strength of the reaction mixture are calculated by a mass balance calculation. In one embodiment of the present invention, an initial brine charge is introduced to the reaction mixture, based on this mass balance calculation, that will maintain the pH and the brine strength at the desired levels throughout the entire reaction. Alternatively, the pH and brine strength of the reaction mixture may be controlled by varying the amounts and concentration of the metal hydroxide which can be added throughout the reaction. The metal hydroxide may be added as a powder to the reaction mixture, however, it is preferable that the metal hydroxide is added as a solution. In accordance with an embodiment of the method of the present invention, the method of measuring the pH and brine strength of the reaction mixture may be accomplished by drawing a sample from the reaction mixture via a slip stream and performing the adequate measurements required and making the required addition of the metal hydroxide solution. The method of adjusting the concentration of the metal hydroxide solution added to the reaction mixture is not particularly limited and may be accomplished by the following non-limiting examples:

(1) having numerous tanks containing different concentration metal hydroxide solutions and choosing an amount from any one or combination of tanks to be added to the reaction mixture, or (2) diluting with water a concentrated metal hydroxide solution in a sufficient amount to provide the desired concentration and amount of metal hydroxide solution.

In preparing the reaction mixture, the reactants are added together such that the presence of the phosgene reactant and water that is not in the form of brine is eliminated or kept to a minimum. Beyond this requirement, the order of addition is not critical. Non-limiting examples of forming the reaction mixture are illustrated below:

(1) combining the reactants of the organic phase (phosgene, an ester-substituted phenol, an organic solvent and catalyst) and then starting the reaction by the addition of brine, (2) combining the ester-substituted phenol, organic solvent, catalyst and brine and then introducing phosgene, (3) combining the ester-substituted phenol, organic solvent, brine, and phosgene and then introducing the catalyst, (4) combining the phosgene, organic solvent, catalyst and brine, and then introducing ester-substituted phenol, and (5) combining the ester-substituted phenol, organic solvent, catalyst and then metering in phosgene and brine to start the reaction.

By conducting the formulation in any of these ways, such that phosgene is not significantly exposed to water that is not in the form of brine during the initial formation of the reaction mixture is referred to herein as being a reaction mixture and process that are "free of water of formulation." "Not significantly exposed" means that the time of exposure and amount of exposure result in minimized degradation of phosgene. Thus, "water of formulation" is distinct from the use of brine in formulation.

According to the method of the present invention, the brine strength of the reaction mixture is maintained during at least a portion of the reaction time between 15% and a saturated brine solution and more preferably between 20% and 25%. The purpose of controlling the brine strength of the reaction mixture is to maximize the conversion of the ester-substituted phenol to a salt so as to efficiently react with the phosgene. It is preferable that the brine strength of the reaction mixture is maintained at this high concentration for as much of the reaction as possible.

The reaction mixture is maintained during at least a portion of the reaction time of phosgene and the ester-substituted phenol at a pH of at least 9.0. (See FIGS. 1, 2, and 3). The purpose of controlling the pH at a high pH during the reaction is because the rates of formation of the product ester-substituted diaryl carbonate drop dramatically when the pH is below 9.0. Thus it is preferable that the pH of the reaction mixture is maintained at a pH of at least 9.0 for as much of the reaction as possible. In one embodiment of the present invention the pH of the reaction mixture is maintained at between 9.0 and 13.5, and more preferably between 11 and 13.5.

A solvent is added to the reaction mixture. It is preferable that the solvent is an organic solvent wherein the organic solvent is a halogenated or non-halogenated solvent. A preferred organic solvent is methylene chloride while a preferred non-halogenated solvent is toluene.

The ester-substituted phenol is contacted with the phosgene for a contact time of sufficient length to allow conversion of the ester-substituted phenol to the product ester-substituted diaryl carbonate. It is preferable that the contact time of the phosgene and the ester-substituted phenol be of sufficient length to convert between 10% and 100% of the ester-substituted phenol to ester-substituted diaryl carbonate product. It is preferable that the conversion be greater than 90% and most preferably greater than 99%. In one embodiment of the present invention the contact time, to produce greater than 90% conversion, is in a range between 5 minutes and 60 minutes. In yet another embodiment of the present invention in which phosgene is added to a solution of the ester-substituted phenol reaction times are limited by the rate of phosgene addition.

The contact between the ester-substituted phenol and phosgene may take place at below ambient temperature, ambient temperature or above ambient temperature. In one embodiment of the present invention ester-substituted phenol is contacted with phosgene at a temperature of between 0° C. and 50° C. preferably between 10° C. and 40° C.

The method of the present invention may at times result in a product mixture comprising ester-substituted diaryl carbonate and the intermediate ester-substituted phenyl chloroformate. It has been found that adding a tertiary amine catalyst to the reaction mixture toward the end of the initial phosgene addition will force the intermediate ester-substituted phenyl chloroformate intermediate toward conversion to the product ester-substituted diaryl carbonate. It has also been found that after this secondary catalyst addition that an additional phosgene addition will drive the reaction mixture to over 99% conversion in a shorter period of time than would be observed without the secondary addition of catalyst. This late addition of a tertiary amine catalyst and phosgene is optional and it has been found to increase the rate of condensation of ester-substituted phenyl chloroformate to ester-substituted diaryl carbonate. Hence the present invention provides a method for producing an ester-substituted diaryl carbonate and an ester-substituted diaryl carbonate formed from the method comprising the steps of:

(a) forming a first reaction mixture comprising phosgene, an ester-substituted phenol, an organic solvent, and a catalyst selected from the group consisting of a tertiary amine catalyst and a phase transfer catalyst, said first reaction mixture having an organic phase and an aqueous phase, wherein the first reaction mixture is formed with less than 15% water of formulation, (b) forming a second reaction mixture by allowing the first reaction mixture to react wherein during the reaction,
 (i) the aqueous phase has a pH, and the pH is adjusted, if necessary, by the addition of an alkali metal hydroxide solution in amounts such that the pH is greater than or equal to 9.0 during at least some portion of the reaction, and
 (ii) the aqueous phase has brine strength, and the brine strength of the aqueous phase is adjusted, if necessary, by varying the concentration of the alkali metal hydroxide solution being added to maintain the pH such that the brine strength is between 15% and a saturated brine solution during at least some portion of the reaction, (c) adding to the second reaction mixture at least 0.50 mole % of a tertiary amine catalyst per mole of ester-substituted phenol introduced to the first reaction mixture, (d) allowing the second reaction mixture to react, wherein the second reaction mixture has an organic phase and an aqueous phase, wherein said aqueous phase has a pH and a brine strength, and wherein during the reaction of the second reaction mixture,
 (i) the pH of the aqueous phase is adjusted, if necessary, by the addition of an alkali metal hydroxide solution in amounts such that the pH is greater than or equal to 9.0 during at least some portion of the reaction to form the second reaction mixture, and
 (ii) the brine strength of the aqueous phase is adjusted, if necessary, by varying the concentration of the alkali metal hydroxide solution being added to maintain the pH such that the brine strength is between 15% and a saturated brine solution during at least some portion of the reaction of the second reaction mixture, thereby forming an ester-substituted diaryl carbonate, wherein the brine strengths of the first and second reaction mixtures are maintained at or above 15% and the pHs of the first and second reaction mixture are maintained at or above 9 for a sufficient portion of the process that the ester-substituted diaryl carbonate is formed with a conversion of at least 90% and a selectivity of at least 98%.

Typically, the amount of ester-substituted phenyl chloroformate is low, less than 1 mole percent based upon the total number of moles of ester-substituted phenol employed, but its presence in the product is undesirable. A small amount of a tertiary amine and an additional charge of phosgene added toward the end of the phosgenation step provides an efficient means for converting residual chloroformates to product. The amount of tertiary amine catalyst used in this secondary catalyst addition is at least 0.50 mole percent based upon the total number of moles of ester-substituted phenol employed. It has also been found that after the secondary addition of catalyst an additional 0.075 mole % of phosgene, per mole of ester-substituted phenol introduced to the first reaction mixture, is introduced to the reaction mixture to increase the rate of formation of ester-substituted diaryl carbonate.

As detailed above the unexpected benefit of the method of the present application is that by reacting the phosgene and the ester-substituted phenol in an environment that is substantially free of water of formulation and in the high pH and brine conditions described herein, a high level of selectivity and conversion of ester-substituted phenol to the product ester-substituted diaryl carbonate is achieved. The prior art processes of producing ester-substituted diaryl carbonates are less desirable than the present invention in that they have lower levels of conversion with higher levels of undesirable by-product formation. One of the major undesirable by-products of producing ester-substituted diaryl carbonates is the trimer of the ester-substituted phenol. The trimer is of the formula:

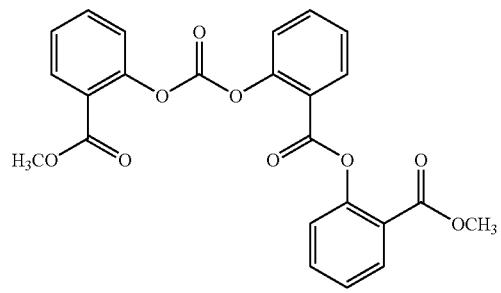

The present invention provides the benefit of minimizing this trimer formation while maximizing conversion. Preferably the present invention provides a process wherein the selectivity is greater than 98% and more preferably greater than 99%. The selectivity is calculated as (mole ester-substituted phenol converted to mole ester-substituted diaryl carbonate/total mole of ester-substituted phenol consumed).

EXAMPLES

Having described the invention in detail, the following examples are provided. The examples should not be considered as limiting the scope of the invention, but merely as illustrative and representative thereof. In reference to the examples the following calculations were made:

"Selectivity" refers to the amount of ester-substituted phenol that is converted to product ester-substituted diaryl carbonate rather than to the undesired by products. It is calculated as (mole ester-substituted phenol converted to mole ester-substituted diaryl carbonate/total mole of ester-substituted phenol consumed).

"Conversion" refers to the total amount of product formed from the raw material ester-substituted phenol. It is calculated as (weight ester-substituted diaryl carbonate/(weight ester-substituted diaryl carbonate+weight ester-substituted phenol+wt by-product)).

"Water of formulation" is also known as free water of formulation and is calculated herein as the weight percent of water based on the weight of dichloromethane in formulation.

Equipment:

A 2-liter glass reactor was fitted with twin 6-blade impellers, a recirculation loop, a reflux condenser, and ports for adding $COCl_2$, and NaOH solution. A pH electrode was mounted in the recirculation loop.

Example 1 (Comparative)

The reactor was charged with 500 ml of methylene chloride, 350 ml of water, methyl salicylate (213 g, 1.40 moles), and triethylamine (1.42 g, 0.014 moles). Phosgene (83.1 g, 0.84 moles) was added at a rate of 2.77 g/min for 30 minutes, and 50% sodium hydroxide was added at 6.72 g/min until phosgene total was 70 g, then raising the rate to 8.96 g/min for the remainder of reaction. A total of 209 g sodium hydroxide solution was used.

Example 2 (Comparative)

The reactor was charged with 500 mL of methylene chloride, 278 mL of water, methyl salicylate (213 g, 1.40 moles), and triethylamine (1.42 g, 0.014 moles). Phosgene (103.9 g, 1.05 moles) was added at a rate of 3.46 g/min for 30 min. 50% sodium hydroxide was added at a rate sufficient to maintain a pH of about 12 during the reaction; a total of 218 g of sodium hydroxide solution was used.

Example 3 (Invention)

The reactor was charged with 500 ml of methylene chloride, methyl salicylate (213 g, 1.40 moles), and triethylamine (1.42 g, 0.014 moles). No water was used in this formulation. Phosgene (103.9 g, 1.05 moles) was added at a rate of 3.46 g/min for 30 min. 22% sodium hydroxide was added at a rate sufficient to maintain a pH of about 12 during the reaction; a total of 469 g of sodium hydroxide solution was used.

Example 4 (Invention)

The reactor was charged with 500 ml of methylene chloride, methyl salicylate (213 g, 1.40 moles), and triethylamine (0.033 g, 0.00033 moles). No water was used in this formulation. Phosgene (90 g, 0.91 moles) was added at a rate of 3.46 g/min for 26 min. 22% sodium hydroxide was added at a rate of 12.72 g/min until about 300 g had been added, then added at a variable rate sufficient to maintain pH of about 12. A total of 346 g of sodium hydroxide solution was used. After the addition of 86.5 g of phosgene, an additional amount of triethylamine (0.73 g, 0.0072 mole) was added to the reaction.

Example 5 (Invention)

The reactor was charged with 470 ml of methylene chloride, methyl salicylate (246 g, 1.617 moles), and triethylamine (0.062 g, 0.00062 moles). No water was used in this formulation. Phosgene (104 g, 1.05 moles) was added at a rate of 4.0 g/min for 26 min. 22% sodium hydroxide was added at a rate of 15.44 g/min until about 385 g had been added, then added at a variable rate sufficient to maintain pH of about 12. A total of 433 g of sodium hydroxide solution was used. After the addition of 91.1 g of phosgene, an additional amount of triethylamine (1.6 g, 0.016 mole) was added to the reaction.

Example 6 (Invention)

The reactor was charged with 470 ml of methylene chloride, methyl salicylate (246 g, 1.617 moles), and triethylamine (0.031 g, 0.00031 moles). No water was used in this formulation. Phosgene (104 g, 1.05 moles) was added at a rate of 4.0 g/min for 26 min. 22% sodium hydroxide was added at a rate of 15.44 g/min until about 337 g had been added, then added at a variable rate sufficient to maintain pH of about 12. A total of 435 g of sodium hydroxide solution was used. After the addition of 91.1 g of phosgene, an additional amount of triethylamine (1.6 g, 0.016 mole) was added to the reaction.

Example 7 (Invention)

The reactor was charged with 500 ml of methylene chloride, methyl salicylate (213 g, 1.40 moles), and methyltributylammonium chloride (4.4 g of 75% aqueous solution, 0.014 moles). No water was used in this formulation. Phosgene (83.1 g, 0.84 moles) was added at a rate of 3.46 g/min for 24 min. 22% sodium hydroxide was added at a rate of 13.99 g/min until a total of 335 g of sodium hydroxide solution was used. 1 minute after phosgene addition was complete, triethylamine (1.42 g, 0.014 moles) was added and reaction stirred an additional 6 minutes.

Example 8 (Invention)

The reactor was charged with 470 ml of methylene chloride, methyl salicylate (246 g, 1.617 moles), and triethylamine (0.031 g, 0.00031 moles). No water was used in this formulation. Phosgene (112 g, 1.13 moles) was added at a rate of 4.0 g/min for 28 min. 22% sodium hydroxide was added at a variable rate sufficient to maintain pH of about 9.2. A total of 457 g of sodium hydroxide solution was used. After the addition of 104 g of phosgene, an additional amount of triethylamine (1.6 g, 0.016 mole) was added to the reaction.

Example 9 (Invention)

The reactor was charged with 470 ml of methylene chloride, methyl salicylate (246 g, 1.617 moles), and triethylamine (0.031 g, 0.00031 moles). No water was used in this formulation. Phosgene (112 g, 1.13 moles) was added at a rate of 4.0 g/min for 28 min. 22% sodium hydroxide was added at a variable rate sufficient to maintain pH of about 10.2. A total of 476 g of sodium hydroxide solution was used. After the addition of 104 g of phosgene, an additional amount of triethylamine (1.6 g, 0.016 mole) was added to the reaction.

Example 10 (Invention)

The reactor was charged with 470 ml of methylene chloride, methyl salicylate (246 g, 1.617 moles), and triethylamine (0.031 g, 0.00031 moles). No water was used in this formulation. Phosgene (112 g, 1.13 moles) was added at a rate of 4.0 g/min for 28 min. 22% sodium hydroxide was added at a variable rate sufficient to maintain pH of about 11. A total of 505 g of sodium hydroxide solution was used. After the addition of 104 g of phosgene, an additional amount of triethylamine (1.6 g, 0.016 mole) was added to the reaction.

Example 11 (Invention)

The reactor was charged with 470 ml of methylene chloride, 100 ml water, sodium chloride (31.54 g), methyl salicylate (213 g, 1.4 moles), and triethylamine (0.054 g, 0.00053 moles). Phosgene (93.5 g, 1.05 moles) was added at a rate of 3.46 g/min for 27 min. 22% sodium hydroxide was added at a rate of 14.1 g/min until about 422 g had been added, then added at a variable rate sufficient to maintain pH of about 12. A total of 433 g of sodium hydroxide solution was used. After the addition of 86.5 g of phosgene, an additional amount of triethylamine (1.42 g, 0.014 mole) was added to the reaction.

RESULTS—Examples 1-11

The results of examples 1-11 are summarized in Table 1 below. Comparative examples 1 and 2 demonstrate that adverse effect of water of formulation upon the conversion and selectivity of the ester-substituted phenol into ester-substituted diaryl carbonate. Invention examples 3-11 demonstrate the present invention in that by minimizing the free water of formulation and controlling the pH and brine strength at high levels during the reaction of the reaction mixture, conversion and selectivity of the ester-substituted phenol into ester-substituted diaryl carbonate is achievable.

TABLE 1

| Ex. # | Initial H₂O of Formulation | Catalyst | Cat. Mole % In Initial Reaction Mix | Cat. ppm in MeCl₂ | pH | Conversion | Selectivity | Final Brine Strength | Caustic Stength |
|---|---|---|---|---|---|---|---|---|---|
| *1 | High | TEA | 1.000 | 2850 | 12.0 | 54.0 | 98.9 | 18 | 50 |
| *2 | Low | TEA | 1.000 | 2138 | 12.0 | 74.0 | 98.4 | 24 | 50 |
| 3 | None | TEA | 1.000 | 2138 | 12.3 | 93.9 | 99.7 | 24 | 22 |
| 4 | None | TEA | 0.023 | 50 | 12.6 | 99.9 | 99.8 | 24 | 22 |
| 5 | None | TEA | 0.038 | 100 | 12.6 | 99.4 | 99.8 | 18 | 22 |
| 6 | None | TEA | 0.019 | 50 | 11.6-13.0 | 99.8 | 99.7 | 28 | 22 |
| 7 | None | PTC + TEA | 1.000 | 5000 | 11.5-13.3 | 99.8 | 99.6 | 27 | 22 |
| 8 | None | TEA | 0.019 | 50 | 9.2 | 99.8 | 99.6 | 28 | 22 |
| 9 | None | TEA | 0.019 | 50 | 10.2 | 99.8 | 99.4 | 28 | 22 |
| 10 | None | TEA | 0.019 | 50 | 11.0 | 99.7 | 99.4 | 28 | 22 |
| 11 | Brine | TEA | 0.038 | 100 | 11.2-12.5 | 99.8 | 99.2 | 26 | 22 |

*Comparative Examples

Examples 12-20

In examples 12-20 BMSC was prepared at pH values of 8, 9, and 10 and at brine strength values of 10, 15, and 22 percent. No water of formulation was added to the reaction mixtures during formulation thereof. The conversion results are summarized in Tables 3, 4, and 5, and in FIGS. 1, 2, and 3. Selectivity values of the ester-substituted phenol into ester-substituted diaryl carbonate were calculated and are shown in Table 2.

As shown in Table 3 and FIG. 1 wherein the reaction was carried out at a pH of 8 and various brine strengths, high levels of conversion were not obtained. However, at pH values of 9 and 10 the desired conversions were obtained. (See Tables 4 and 5 and FIGS. 2 and 3).

Examples 12-20 all achieved selectivity values of 99% or higher (see Table 2). Selectivity, as shown in Table 2, increases with the brine concentration at constant pH. Further, selectivity decreases with an increase of pH at a constant brine concentration.

TABLE 2

Selectivity Data for Examples 12-20

| PH | Brine Concentration | | |
|---|---|---|---|
| | 10 | 15 | 22 |
| 8 | 99.7 | 99.8 | 99.9 |
| 9 | 99.5 | 99.6 | 99.8 |
| 10 | 99.2 | 99.4 | 99.6 |

TABLE 3

Conversion Data for Examples 12-14
Examples 12-14: MS Conversion @ pH 8 and Various Brine Conentrations

| Time (min) | Phos Amt | 10% NaOH | 15% NaOH | 22% NaOH |
|---|---|---|---|---|
| 20 | 1.0 | 39.05 | 47.82 | 73.44 |
| 22 | 1.1 | 33.20 | 50.14 | 71.53 |
| 24 | 1.2 | 35.48 | 52.58 | 77.31 |
| 26 | 1.3 | 37.42 | 54.41 | 76.15 |
| 28 | 1.4 | 37.42 | 54.41 | 76.15 |

TABLE 4

Conversion Data for Examples 15-17
Examples 15-17: MS Conversion @ pH 9 and Various Brine Conentrations

| Time (min) | Phos Amt | 10% NaOH | 15% NaOH | 22% NaOH |
|---|---|---|---|---|
| 20 | 1.0 | 40.48 | 62.59 | 78.61 |
| 22 | 1.1 | 44.30 | 62.37 | 85.38 |
| 24 | 1.2 | 46.20 | 63.45 | 91.05 |
| 26 | 1.3 | 47.68 | 66.64 | 93.31 |
| 28 | 1.4 | 57.68 | 66.64 | 93.31 |
| 33 | 1.5 | 51.27 | 69.53 | 97.46 |

TABLE 5

Conversion Data for Examples 18-20
Examples 18-20: MS Conversion @ pH 10 and Various Brine Conentrations

| Time (min) | Phos Amt | 10% NaOH | 15% NaOH | 22% NaOH |
|---|---|---|---|---|
| 20 | 1.0 | 45.77 | 69.16 | 83.72 |
| 22 | 1.1 | 49.72 | 78.88 | 89.57 |
| 24 | 1.2 | 52.54 | 74.16 | 94.67 |
| 26 | 1.3 | 55.69 | 82.67 | 98.52 |
| 28 | 1.4 | 55.69 | 82.67 | 98.52 |
| 33 | 1.5 | 59.27 | 79.36 | 99.85 |

Examples 21-26

In examples 21-26 BMSC was prepared in accordance with the present invention at a pH greater than 9 and at brine strength of greater than 15 percent. Water of formulation was added to the reaction mixtures during formulation thereof in the amounts indicated in tables 6 and 7. Conversions were calculated throughout the process runs and are summarized in Table 6 and in FIG. 4. Selectivity values of the ester-substituted phenol into ester-substituted diaryl carbonate were calculated and are shown in Table 7 and in FIG. 5 as a function of weight percent trimer formation during the process runs.

As shown in Tables 6 and 7 and in FIGS. 4 and 5, up to 15 percent water of formulation may be present in the reaction mixture and still achieve 90% conversion and 98% selectivity.

Examples 21-26 demonstrate that by minimizing the water of formulation, the conversion of the ester-substituted phenol to ester-substituted diaryl carbonate is maximized while minimizing by-product formation.

TABLE 6

(Examples 21-26) Methyl salicilate conversion % data using different water of formulations

| | Ex. # (% WF)* | | | | | |
|---|---|---|---|---|---|---|
| | 21 (0.0%) | 22 (0.5%) | 23 (2.0%) | 24 (5.0%) | 25 (10.0%) | 26 (15.0%) |
| 4 (minutes) | 27.07 | 22.56 | 20.46 | 24.29 | 15.42 | 19.53 |
| 8 | 46.38 | 40.11 | 38.60 | 37.83 | 32.78 | 33.01 |
| 12 | 65.06 | 58.78 | 56.55 | 53.60 | 48.05 | 49.04 |
| 16 | 79.05 | 77.17 | 73.26 | 71.08 | 61.94 | 62.89 |
| 18 | 88.28 | 86.43 | 81.54 | 79.27 | 69.35 | 70.31 |
| 20 | 97.36 | 94.45 | 91.06 | 88.68 | 75.43 | 76.42 |
| 22 | 99.45 | 98.82 | 97.93 | 97.24 | 83.59 | 79.40 |
| 24 | | 99.48 | 99.39 | 99.47 | 90.80 | 84.25 |
| 26 | 99.63 | 99.91 | 99.88 | 99.82 | 95.83 | 89.75 |
| 31 | 99.85 | 99.90 | 99.83 | 99.87 | 96.31 | 90.30 |
| 36 | 99.88 | 99.87 | 99.86 | 99.84 | 96.28 | 90.46 |
| 46 | 99.84 | 99.88 | 99.84 | 99.83 | 96.20 | |

*(% WF) = % Water of formulation

TABLE 7

(Examples 21-26) Selectivity data calculated in weight % trimer formation using different water of forumulations

| | Ex. # (% WF)* | | | | | |
|---|---|---|---|---|---|---|
| | 21 (0.0%) | 22 (0.5%) | 23 (2.0%) | 24 (5.0%) | 25 (10.0%) | 26 (15.0%) |
| 4 (minutes) | 0.00 | 0.00 | 0.00 | 0.00 | 0.00 | 0.00 |
| 8 | 0.00 | 0.00 | 0.05 | 0.07 | 0.09 | 0.09 |
| 12 | 0.09 | 0.00 | 0.07 | 0.11 | 0.12 | 0.19 |
| 16 | 0.11 | 0.11 | 0.12 | 0.18 | 0.18 | 0.36 |
| 18 | | | 0.16 | 0.21 | 0.24 | 0.50 |
| 20 | 0.18 | 0.23 | 0.19 | 0.27 | 0.30 | 0.55 |
| 22 | 0.28 | 0.20 | | 0.31 | 0.35 | 0.56 |
| 24 | | 0.28 | 0.28 | 0.40 | 0.45 | 0.63 |
| 26 | 0.24 | 0.28 | 0.33 | 0.45 | 0.60 | 0.81 |
| 31 | 0.27 | 0.32 | 0.37 | 0.47 | 0.58 | 0.84 |
| 36 | 0.26 | 0.30 | 0.36 | 0.49 | 0.59 | |
| 46 | 0.27 | 0.33 | 0.35 | 0.46 | | |

*(% WF) = % Water of formulation

The invention claimed is:

1. A method for preparing an ester-substituted diaryl carbonate comprising the steps of:
   (a) forming a reaction mixture comprising phosgene, an ester-substituted phenol, an organic solvent, and a catalyst selected from the group consisting of a tertiary amine catalyst and a phase transfer catalyst, said reaction mixture having an organic phase and an aqueous phase, wherein said aqueous phase has a brine strength,
   (b) allowing the reaction mixture to react wherein during the reaction,
      (i) the aqueous phase has a pH, and the pH is adjusted, if necessary, by the addition of an alkali metal hydroxide solution in amounts such that the pH is greater than or equal to 9.0 during at least some portion of the reaction, and
      (ii) the brine strength of the aqueous phase is adjusted, if necessary, by varying the concentration of the alkali metal hydroxide solution being added to maintain the pH such that the brine strength is between 15% and a saturated brine solution during at least some portion of the reaction,
   thereby forming an ester-substituted diaryl carbonate, wherein the reaction mixture is formed with less than 15% water of formulation, and wherein the brine strength is maintained at or above 15% and the pH is maintained at or above 9 for a sufficient portion of the process that the ester-substituted diaryl carbonate is formed with a conversion of at least 90% and a selectivity of at least 98%.

2. The method of claim 1, wherein the catalyst selected is a tertiary amine and the tertiary amine catalyst and the ester-substituted phenol are introduced to the reaction mixture in a mole ratio of between 0.01-0.09.

3. The method of claim 1, wherein the ester-substituted phenol and the phosgene are introduced to the reaction mixture in a mole ratio of between 0.50 to 1.00 and 0.75 to 1.00 moles of phosgene to moles of ester-substituted phenol.

4. The method of claim 1, wherein during the reaction of the reaction mixture the brine strength is in a range between 20% and 25% for at least a portion of the reaction.

5. The method of claim 1, wherein the portion of the reaction during which the brine strength is greater than 15% and the pH is greater than 9 is sufficient to achieve a conversion greater than 98%.

6. The method of claim 1, wherein during the reaction of the reaction mixture, the phosgene and ester-substituted phenol are contacted for a length of time sufficient to convert between 10% and 100% of the ester-substituted phenol to ester-substituted diaryl carbonate.

7. The method of claim 1, wherein the ester-substituted diaryl carbonate has the structure,

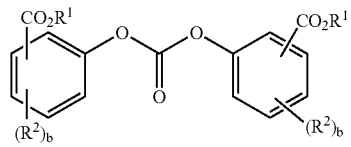

wherein $R^1$ is independently at each occurrence a $C_1$-$C_{20}$ alkyl radical, $C_4$-$C_{20}$ cycloalkyl radical, or $C_4$-$C_{20}$ aromatic radical; $R^2$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and b is independently at each occurrence an integer 0-4.

8. The method of claim 7, wherein the ester-substituted diaryl carbonate is bis-methylsalicyl carbonate.

9. The method of claim 1, wherein ester-substituted phenol has structure,

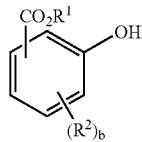

wherein $R^1$ is $C_1$-$C_{20}$ alkyl radical, $C_4$-$C_{20}$ cycloalkyl radical or $C_4$-$C_{20}$ aromatic radical, $R^2$ is independently at each occurrence a hydrogen atom, halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, and $C_1$-$C_{20}$ acylamino radical; and b is an integer 0-4.

10. The method of claim 9, wherein the ester-substituted phenol is selected from the group consisting of phenyl salicylate, methyl salicylate, ethyl salicylate, isopropyl salicylate and benzyl salicylate.

11. The method of claim 1, wherein the tertiary amine catalyst has structure,

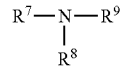

wherein each $R^7$, $R^8$, and $R^9$ are independently a $C_1$-$C_{18}$ alkyl group, a $C_3$-$C_{18}$ cycloalkyl group, or $R^7$, $R^8$, and $R^9$ together form a $C_4$-$C_{20}$ cycloaliphatic ring which may be substituted by one or more $C_1$-$C_{20}$ alkyl, $C_6$-$C_{20}$ aryl, $C_5$-$C_{21}$ aralkyl, $C_5$-$C_{20}$ cycloalkyl groups or a combination thereof.

12. The method of claim 11, wherein the tertiary amine catalyst is selected from the group consisting of triethylamine, dimethylbutylamine, diisopropylethylamine, tributylamine, and 1,4-diazabicyclooctane.

13. The method of claim 12, wherein the tertiary amine catalyst is triethylamine.

14. The method of claim 1, wherein the catalyst selected is a phase transfer catalyst and has the structure,

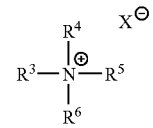

wherein $R^3$-$R^6$ are independently a $C_1$-$C_{20}$ alkyl radical, $C_4$-$C_{20}$ cycloalkyl radical, or a $C_4$-$C_{20}$ aryl radical, and $X^-$ is an organic or inorganic anion.

15. The method of claim 14, wherein the phase transfer catalyst is selected from the group consisting of tetramethyl ammonium hydroxide, tetrabutyl ammonium hydroxide, tetramethyl ammonium acetate, tetramethyl ammonium formate, tetrabutyl ammonium acetate, methyl tributyl ammonium chloride, tetramethyl ammonium hydroxide, tetrabutyl ammonium chloride and decyl trimethyl ammonium chloride.

16. The method of claim 14, wherein the phase transfer catalyst is methyl tributyl ammonium chloride.

17. The method of claim 1, wherein during the reaction of the reaction mixture the pH is between 11 and 13.5 for at least a portion of the reaction.

18. The method of claim 1, wherein the alkali metal hydroxide is sodium hydroxide.

19. The method of claim 1, wherein the reaction mixture is formed with less than 10% water of formulation.

20. The method of claim 1, wherein the reaction mixture is formed with less than 5% water of formulation.

21. The method of claim 1, wherein the reaction mixture is formed with no water of formulation.

* * * * *